United States Patent
Laughner et al.

(10) Patent No.: US 11,369,428 B2
(45) Date of Patent: Jun. 28, 2022

(54) SMART POWER SELECTION FOR MULTI-ELECTRODE RF ABLATION SYSTEM

(71) Applicant: Boston Scientific Scimed Inc., Maple Grove, MN (US)

(72) Inventors: Jacob I. Laughner, St. Paul, MN (US); Jeffry V. Marshik, New Brighton, MN (US); Randall Dodson, New Hope, MN (US); Kara Garrott, Minneapolis, MN (US); Dustin J. Olynyk, Eagan, MN (US); Kimberly A. Miklos, Plymouth, MN (US); Melissa R. McMahon, Minneapolis, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 165 days.

(21) Appl. No.: 16/774,068

(22) Filed: Jan. 28, 2020

(65) Prior Publication Data

US 2020/0237425 A1 Jul. 30, 2020

Related U.S. Application Data

(60) Provisional application No. 62/798,009, filed on Jan. 29, 2019.

(51) Int. Cl.
*A61B 18/12* (2006.01)
*A61B 18/14* (2006.01)
(Continued)

(52) U.S. Cl.
CPC ...... *A61B 18/1206* (2013.01); *A61B 18/1492* (2013.01); *A61B 34/25* (2016.02);
(Continued)

(58) Field of Classification Search
CPC ............... A61B 18/1206; A61B 34/25; A61B 2018/00898; A61B 2018/00666;
(Continued)

(56) References Cited

U.S. PATENT DOCUMENTS

| 2007/0049919 | A1* | 3/2007 | Lee | ......... A61B 18/16 606/34 |
| 2009/0187177 | A1* | 7/2009 | Epstein | ......... A61B 18/16 606/33 |

(Continued)

FOREIGN PATENT DOCUMENTS

WO 2017/184628 * 10/2017 ............ A61B 18/14

*Primary Examiner* — Jaymi E Della (74) *Attorney, Agent, or Firm* — Faegre Drinker Biddle & Reath LLP (57) ABSTRACT

A computing device for generating and using a graphical user interface (GUI) is disclosed. The computing device includes one or more controllers configured to generate a graphical representation of a plurality of electrodes of an ablation catheter for displaying via the GUI; designate, via the GUI, at least some of the plurality of electrodes to be active electrodes; automatically designate the active electrodes as a source electrode or a sink electrode; assign an amount of energy to each of the designated source electrodes; and estimate an amount of energy associated with each of the designated sink electrodes based at least in part on the assigned energy of the designated source electrodes.

17 Claims, 7 Drawing Sheets

(51) Int. Cl.
*A61B 34/00* (2016.01)
*A61B 1/04* (2006.01)
*A61B 1/06* (2006.01)
*A61B 18/00* (2006.01)

(52) U.S. Cl.
CPC ............... *A61B 1/04* (2013.01); *A61B 1/0684* (2013.01); *A61B 2018/0022* (2013.01); *A61B 2018/00577* (2013.01); *A61B 2018/00666* (2013.01); *A61B 2018/00702* (2013.01); *A61B 2018/00898* (2013.01); *A61B 2018/00982* (2013.01); *A61B 2018/126* (2013.01); *A61B 2018/1467* (2013.01)

(58) Field of Classification Search
CPC .... A61B 2018/1467; A61B 2018/0022; A61B 2018/165
See application file for complete search history.

(56) References Cited

U.S. PATENT DOCUMENTS

2013/0138097 A1* 5/2013 Mathur ................. A61B 18/18
606/33
2018/0085163 A1* 3/2018 Zeledon ............ A61B 18/1492

\* cited by examiner

SMART POWER SELECTION FOR MULTI-ELECTRODE RF ABLATION SYSTEM

CROSS REFERENCE TO RELATED APPLICATION

This application claims priority to Provisional Application No. 62/798,009, filed Jan. 19, 2019, which is herein incorporated by reference in its entirety.

TECHNICAL FIELD

The present disclosure relates generally to systems, devices, and methods involving cardiac ablation.

BACKGROUND

Various cardiac abnormalities can be attributed to improper electrical activity of cardiac tissue. Such improper electrical activity can include generation of electrical signals, conduction of electrical signals of the tissue, etc., in a manner that does not support efficient and/or effective cardiac function. For example, an area of cardiac tissue may become electrically active prematurely or otherwise out of synchrony during the cardiac cycle, causing the cardiac cells of the area and/or adjacent areas to contract out of rhythm. The result is an abnormal cardiac contraction that is not timed for optimal cardiac output. In some cases, an area of cardiac tissue may provide a faulty electrical pathway (e.g., a short circuit) that causes an arrhythmia, such as atrial fibrillation or supraventricular tachycardia. In some cases, inactive tissue (e.g., scar tissue) may be preferable to malfunctioning cardiac tissue.

SUMMARY

In Example 1, a computer-implemented method for displaying and using a graphical user interface (GUI) is disclosed. The method includes displaying, via the GUI, a graphical representation of a plurality of electrodes of an ablation catheter; designating, via the GUI, at least some of the plurality of electrodes to be active electrodes; designating the active electrodes as a source electrode or a sink electrode; assigning an electrical unit to each of the designated source electrodes; and estimating an amount of electrical units associated with each of the designated sink electrodes based at least in part on the assigned electrical unit of the designated source electrodes.

In Example 2, the method of Example 1, wherein estimating the electrical units associated with each of the designated sink electrodes is further based at least in part on distances between the designated source electrodes and the designated sink electrodes.

In Example 3, the method of Example 2, wherein the distances between the designated source electrodes and the designated sink electrodes represent edge-to-edge distances.

In Example 4, the method of Examples 2 or 3, wherein the distances are selected from a table of predetermined distances or are computed by one or more controllers.

In Example 5, the method of any of Examples 1-4, wherein estimating the electrical units associated with each of the designated sink electrodes includes adding each source's contribution to sink energy associated with each of the designated sink electrodes.

In Example 6, the method of any of Examples 1-5, further comprising modifying the assigned electrical units to at least one of the designated source electrodes or designating an additional active electrode or inactive electrode; and re-estimating the amount of electrical units associated with each of the designated sink electrodes based at least in part on the modified assigned electrical units of the at least one designated source electrode or the additional active or inactive electrode.

In Example 7, the method of any of Examples 1-6, further comprising determining that the estimated electrical units associated with at least one of the designated sink electrodes is above a threshold; and disabling an ablation-initiation button on the GUI in response to the determination.

In Example 8, the method of any of Examples 6 and 7, further comprising after re-estimating the electrical units associated with each of the designated sink electrodes, determining that the estimated electrical units associated with at least one of the designated sink electrodes is below the threshold; and enabling the ablation-initiation button on the GUI in response to determining that the estimated electrical units associated with at least one of the designated sink electrodes is below the threshold.

In Example 9, the method of any of Examples 1-8, further comprising displaying, via the GUI, the estimated electrical units associated with each of the designated sink electrodes; and displaying, via the GUI, an indicator representing the estimated electrical unit being above or below one or more thresholds.

In Example 10, the method of any of Examples 1-9, further comprising automatically modifying the assigned electrical units to each of the designated source electrodes in response to the estimated electrical units associated with each of the designated sink electrodes.

In Example 11, the method of any of Examples 1-10, further comprising communicating the assigned electrical units or modified assigned electrical units for each of the designated source electrodes to a radio frequency generator.

In Example 12, the method of any of Examples 1-11, wherein the electrical unit is power.

In Example 13, a computing device adapted to execute the steps of the method of Examples 1-12.

In Example 14, a computer program product comprising instructions to cause one or more processors to carry out the steps of the method of Examples 1-12.

In Example 15, a computer-readable medium having stored thereon the computer program product of Example 14.

In Example 16, an ablation system includes a radiofrequency (RF) generator configured to generate RF energy and an ablation catheter in communication with the RF generator and including a plurality of electrodes. The ablation system further includes one or more controllers in communication with the RF generator and configured to: generate a graphical representation of the plurality of electrodes of the ablation catheter for displaying via a graphical user interface (GUI); designate, via the GUI, at least some of the plurality of electrodes to be active electrodes; designate the active electrodes as a source electrode or a sink electrode; assign a power to each of the designated source electrodes; and estimate an amount of power associated with each of the designated sink electrodes based at least in part on the assigned power of the designated source electrodes.

In Example 17, the ablation system of Example 16, wherein the estimated amount of power associated with each of the designated sink electrodes is further based at least in part on distances between the designated source electrodes and the designated sink electrodes.

In Example 18, the ablation system of Example 17, wherein the distances between the designated source electrodes and the designated sink electrodes represent edge-to-edge distances.

In Example 19, the ablation system of any of Examples 17 and 18, wherein the distances are selected from a table of predetermined distances stored in the one or more controllers or computed by the one or more controllers.

In Example 20, the ablation system of any of Examples 16-19, wherein the estimated the amount of power associated with each of the designated sink electrodes is based at least in part on adding each source's contribution to power associated with each of the designated sink electrodes.

In Example 21, the ablation system of any of Examples 16-20, wherein the one or more controllers is configured to: modify the assigned power to at least one of the designated source electrodes or designating an additional electrode as an active electrode or inactive electrode; and re-estimate the amount of power associated with each of the designated sink electrodes based at least in part on the modified assigned power of the at least one designated source electrode or the additional active electrode or inactive electrode.

In Example 22, the ablation system of any of Examples 16-21, wherein the one or more controllers is configured to determine that the estimated power associated with at least one of the designated sink electrodes is above a threshold; and disable an ablation-initiation button on the GUI in response to the determination.

In Example 23, the ablation system of any of Examples 21 and 22, wherein the one or more controllers is configured to after re-estimating the amount of power associated with each of the designated sink electrodes, determine that the estimated power associated with at least one of the designated sink electrodes is below the threshold; and enable the ablation-initiation button on the GUI in response to determining that the estimated power associated with at least one of the designated sink electrodes is below the threshold.

In Example 24, the ablation system of any of Examples 16-23, wherein the ablation catheter includes an expandable member carrying the plurality of electrodes.

In Example 25, the ablation system of any of Examples 16-24, further comprising a display in communication with the one or more controllers and configured to display the GUI.

In Example 26, a computing device for generating and using a graphical user interface (GUI) is disclosed. The computing device includes one or more controllers configured to: generate a graphical representation of a plurality of electrodes of an ablation catheter for displaying via the GUI; designate, via the GUI, at least some of the plurality of electrodes to be active electrodes; automatically designate the active electrodes as a source electrode or a sink electrode; assign an amount of energy to each of the designated source electrodes; and estimate an amount of energy associated with each of the designated sink electrodes based at least in part on the assigned energy of the designated source electrodes.

In Example 27, the computing device of Example 26, wherein the estimated amount of energy associated with each of the designated sink electrodes is further based at least in part on distances between the designated source electrodes and the designated sink electrodes.

In Example 28, the computing device of Example 27, wherein the distances between the designated source electrodes and the designated sink electrodes represent edge-to-edge distances.

In Example 29, the computing device of Example 27, wherein the distances are selected from a table of predetermined distances stored in the one or more controllers.

In Example 30, the computing device of Example 26, wherein the estimated the amount of energy associated with each of the designated sink electrodes is based at least in part on adding each source's contribution to energy associated with each of the designated sink electrodes.

In Example 31, the computing device of any of Examples 26-30, wherein the one or more controllers includes a computer readable storage medium having program code stored thereon for execution by the one or more controllers to carry out the functions of Examples 26-30.

In Example 32, the computing device of Example 26, wherein the one or more controllers is configured to determine that the estimated amount of energy associated with at least one of the designated sink electrodes is above a threshold; and disable an ablation-initiation button on the GUI in response to the determination.

In Example 33, a computing device for generating and using a graphical user interface (GUI) is disclosed. The computing device includes one or more controllers configured to: generate a graphical representation of a plurality of electrodes of an ablation catheter for displaying via the GUI; designate, via the GUI, at least some of the plurality of electrodes to be active electrodes; automatically designate the active electrodes as a source electrode or a sink electrode; and automatically assign a power to each of the designated source electrodes such that an estimated power associated with each of the designated sink electrodes is less than a first predetermined threshold.

In Example 34, the computing device of Example 33, wherein the estimated power of a first set of the sink electrodes is compared against the first predetermined threshold, wherein the estimated power of a second set of the sink electrodes is compared against a second predetermined threshold that is different than the first predetermined threshold.

In Example 35, the computing device of Example 33, further comprising automatically assign a power to each of the designated source electrodes such that an estimated power associated with each of the designated sink electrodes is substantially similar to the estimated power of the other sink electrodes.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Cardiac ablation is a procedure by which cardiac tissue is treated to inactivate the tissue. The tissue targeted for ablation may be associated with improper electrical activity, as described above. Cardiac ablation can create lesions in the tissue and prevent the tissue from improperly generating or conducting electrical signals. For example, lesions in the form of a line or a circle can block the propagation of errant electrical signals. Control of the shape, depth, uniformity, etc., of the lesion is desirable.

Certain embodiments of the present disclosure involve systems, devices, and methods that can be used in connection with cardiac ablation. In particular, the present disclosure describes graphical user interfaces that display and enable control of a graphical representation of features of the ablation catheter. The graphical user interfaces can be used for viewing, selecting, and modifying ablation parameters, among other things. For example, the graphical user interfaces can be used to view, select, and modify ablation patterns and energy associated with ablation electrodes. As such, the graphical user interfaces can be used to help control the shape, depth, and uniformity of lesions.

Figure 1:
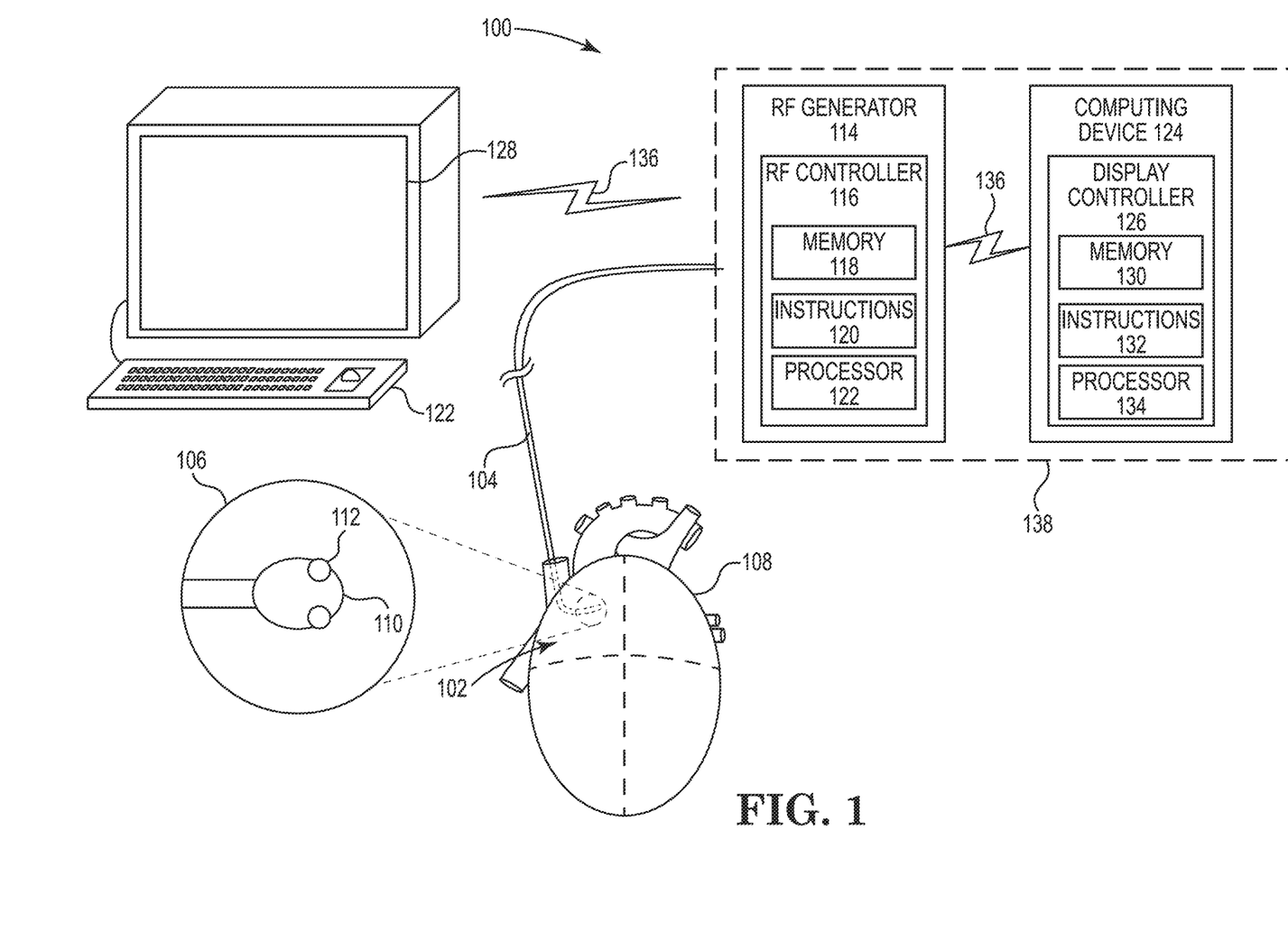
FIG. 1 shows an ablation system, in accordance with certain embodiments of the present disclosure.

FIG. 1 shows an ablation system 100 including an ablation catheter 102 comprising an elongated catheter body 104 and a distal catheter region 106, which is configured to be positioned within a heart 108. The ablation catheter 102 includes an expandable member 110 (e.g., membrane, balloon) and a plurality of energy delivery elements 112 (e.g., ablation electrodes) secured to the expandable member 110. The energy delivery elements 112 are configured and positioned to deliver ablative energy (e.g., radiofrequency energy) to tissue when the expandable member 110 is inflated.

The system 100 includes a radiofrequency (RF) generator 114 electrically coupled to the plurality of energy delivery elements 112 and configured to generate RF energy. The RF generator 114 includes an RF generator controller 116 configured to control the RF energy to the plurality of energy delivery elements 112. The RF generator controller 116 can be implemented using firmware, integrated circuits, and/or software modules that interact with each other or are combined together. For example, the RF generator controller 116 may include memory 118 storing computer-readable instructions/code 120 for execution by a processor 122 (e.g., microprocessor) to perform aspects of embodiments of methods discussed herein.

The system 100 can also include a computing device 124 (e.g., personal computer) with a display controller 126 configured to communicate with various components of the system 100 and generate a graphical user interface (GUI) to be displayed via a display 128 (e.g., computer monitor, television, mobile device screen). The display controller 126 can be implemented using firmware, integrated circuits, and/or software modules that interact with each other or are combined together. For example, the display controller 126 may include memory 130 storing computer-readable instructions/code 132 for execution by a processor 134 (e.g., microprocessor) to perform aspects of embodiments of methods discussed herein.

The various components of the system 100 may be communicatively coupled to each other via communication links 136. In certain embodiments, the communication links 136 may be, or include, a wired communication link (e.g., a serial communication), a wireless communication link such as, for example, a short-range radio link, such as Bluetooth, IEEE 802.11, a proprietary wireless protocol, and/or the like. The term "communication link" may refer to an ability to communicate some type of information in at least one direction between at least two components and may be a persistent communication link, an intermittent communication link, an ad-hoc communication link, and/or the like. The communication links 136 may refer to direct communications between components and/or indirect communications that travel between components via at least one other device (e.g., a repeater, router, hub).

In embodiments, the memory 118 and 130 includes computer-readable storage media in the form of volatile and/or nonvolatile memory and may be removable, non-removable, or a combination thereof. Media examples include Random Access Memory (RAM), Read Only Memory (ROM), Electronically Erasable Programmable Read Only Memory (EEPROM), flash memory, and/or any other non-transitory storage medium that can be used to store information and can be accessed by a computing device. In certain embodiments, the ablation catheter 102 includes memory that stores information unique to the ablation catheter 102 (e.g., catheter ID, manufacturer). This information can be accessed and associated with data collected as part of an ablation procedure (e.g., patient data, ablation parameters).

The computer-executable instructions 120 and 132 may include, for example, computer code, machine-useable instructions, and the like such as, for example, program components capable of being executed by the one or more processors 122 and 134. Some or all of the functionality contemplated herein may be implemented in hardware and/or firmware.

In certain embodiments, the RF generator 114 and the computing device 124 are separate components housed in a single console 138. In certain embodiments, the RF generator 114 and the computing device 124 each include a plurality of controllers that are configured to perform aspects of embodiments of methods and procedures discussed herein.

Figure 2:
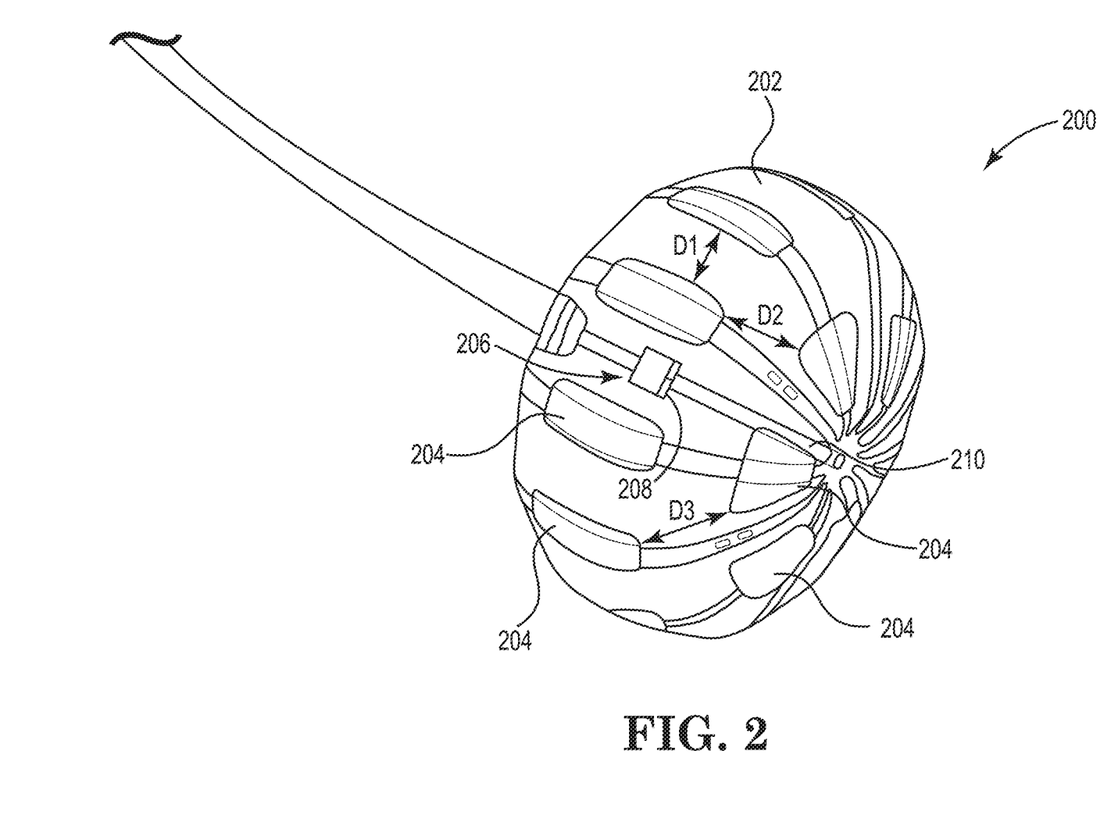
FIG. 2 shows a side, cut-away view of an ablation catheter, in accordance with certain embodiments of the present disclosure.

FIG. 2 shows an ablation catheter 200 that can be used in the system 100. The ablation catheter 200 includes an expandable member 202 and a plurality of energy delivery elements 204 secured to the expandable member 202. The energy delivery elements 204 are configured and positioned to deliver ablative energy to tissue when the expandable member 202 is inflated. As shown in FIG. 2, in certain embodiments, the energy delivery elements 204 are arranged in two rows, one proximal set of energy delivery elements 204 and one distal row of energy delivery elements 204. Each of the energy delivery elements 204 is individually addressable or can be used with any other energy delivery element 204. The energy delivery elements 204 can operate in a monopolar mode or bipolar mode. Sets of energy delivery elements 204 can be chosen such that the lesion is linear, a spot, a hollow circle, etc. In embodiments utilizing a monopolar mode, the system 100 may include a return pad.

The ablation catheter 200 includes a visualization system 206 including a camera assembly 208 and illumination sources (e.g., light-emitting diodes (LEDs)) disposed on a guide wire shaft 210. The camera assembly 208 can include a plurality of cameras disposed at an angle relative to a longitudinal axis of the ablation catheter 200. The cameras are configured to enable real-time imaging (e.g., video) of an ablation procedure from within the expandable member 202 including visualizing the expandable member 202, the energy delivery elements 204, and cardiac tissue as well as lesion formation during the ablation procedure. The illumination sources provide lighting for the cameras to visualize the ablation procedure.

Figure 3:
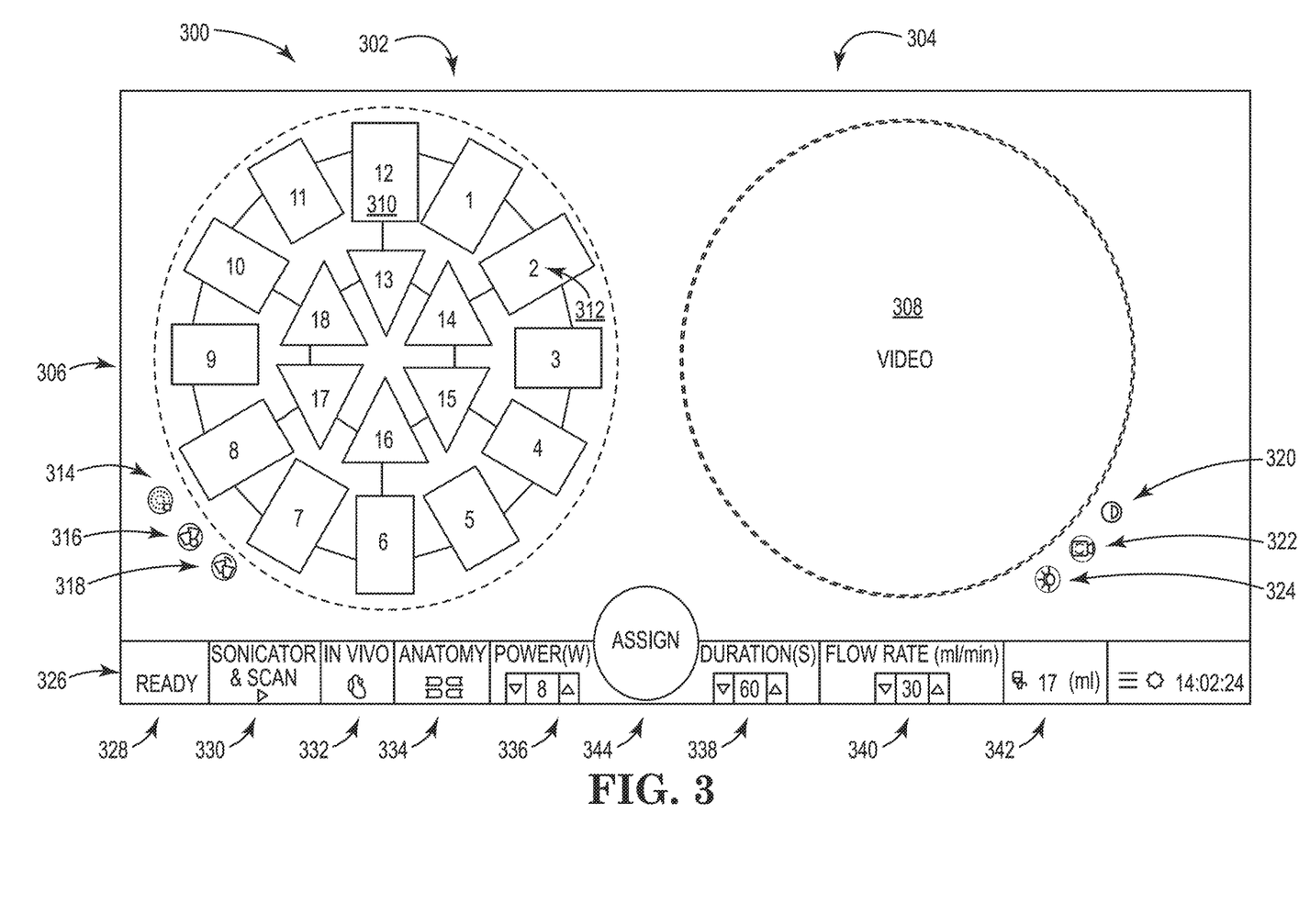
FIGS. 3-5 show various views of a graphical user interface, in accordance with certain embodiments of the present disclosure.
Figure 4:
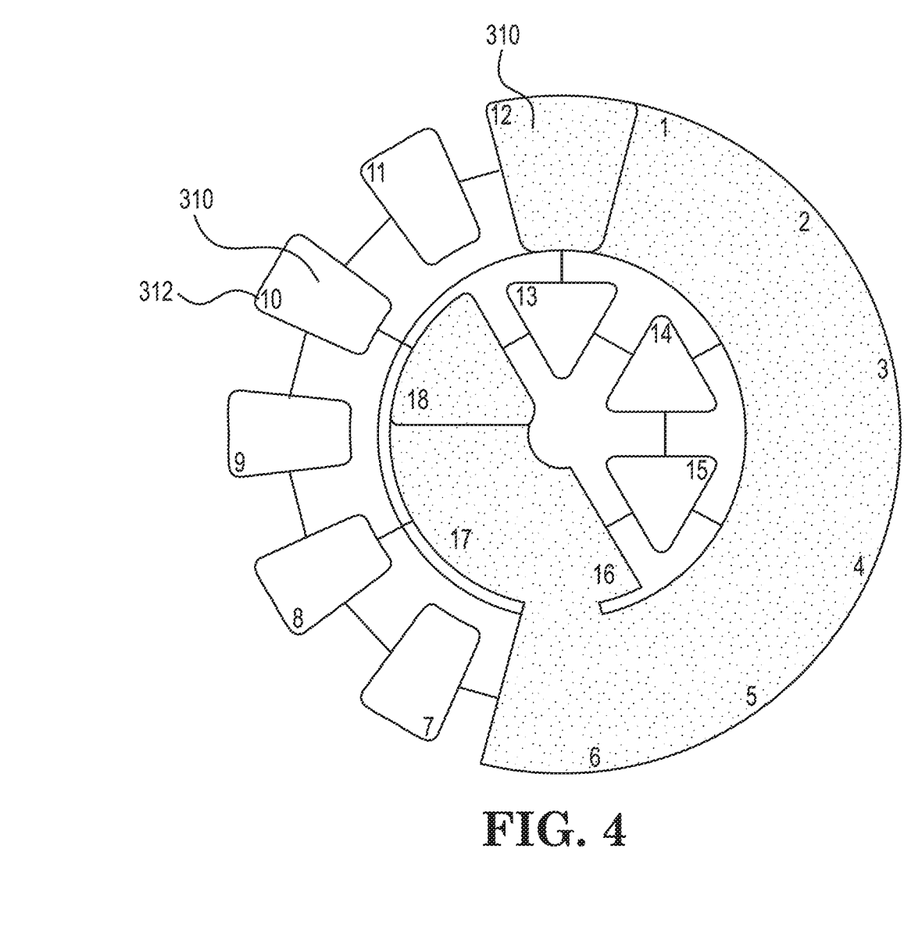
Figure 5:
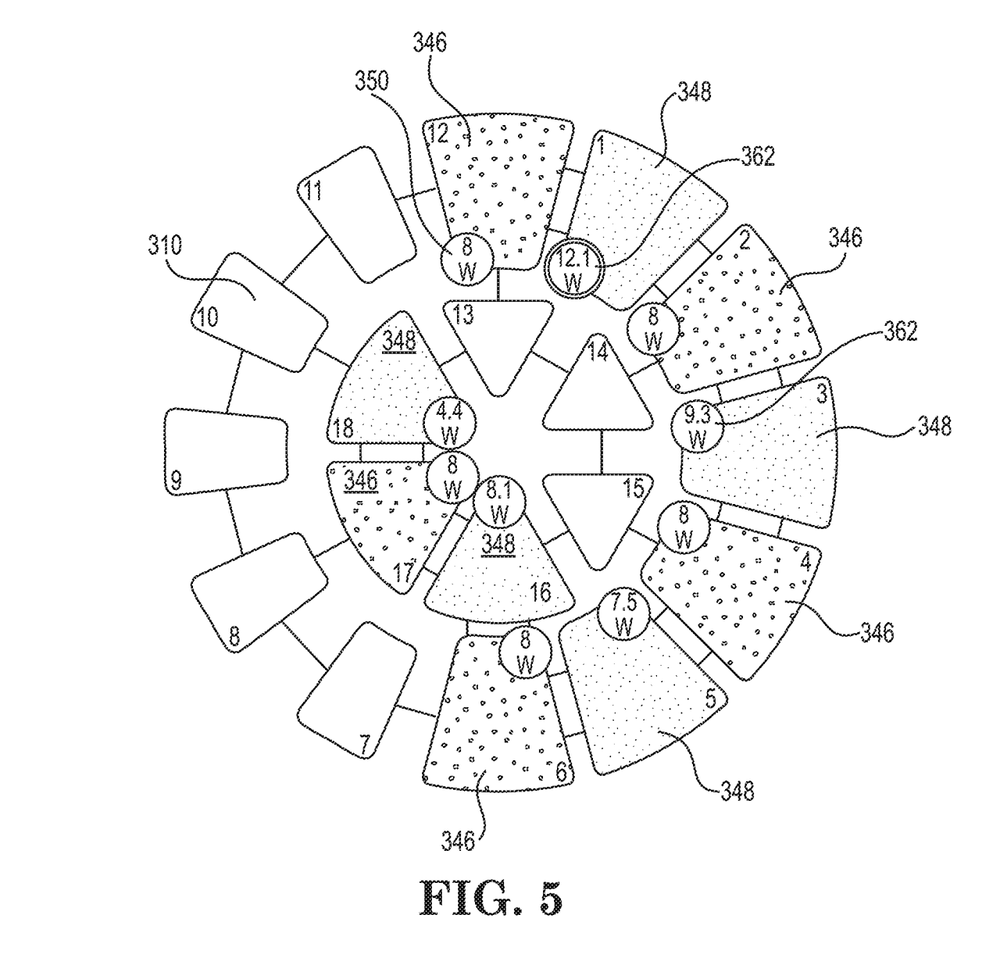

As mentioned above, the computing device 124 of the system 100 includes the display controller 126 that is configured to communicate with various components of the system 100 and generate a GUI for displaying via the display 128. FIGS. 3-5 show an example GUI and its various features and views that can be used in the system 100 and displayed via the display 128. Users can interact (e.g., select icons, enter data) with the GUI using one or more input devices (e.g., mouse, keyboard, touchscreen). The various icons described below can take the form of selectable buttons, indicators, images, etc., on the GUI.

FIGS. 3-5 show a GUI 300 including a first region 302 and a second region 304. The first region 302 displays a graphical representation 306 of electrodes of an ablation catheter, and the second region 304 displays a real-time video 308 from the ablation catheter. The first region 302 and the second region 304 are shown as being positioned side-by-side and being circular-shaped regions. In certain embodiments, the first region 302 and the second region 304 are separate windows within the GUI 300.

The graphical representation 306 includes a separate electrode icon 310 for each of the plurality of electrodes of the ablation catheter. In certain embodiments, each electrode icon 310 is similarly-shaped to an actual shape of a corresponding electrode on the ablation catheter. Each electrode icon 310 can include a unique numerical indicator 312. For example, in the embodiment shown in FIGS. 3-5, the ablation catheter being represented by the graphical representation 306 includes twelve electrodes in an outer ring and six electrodes in an inner ring, and each of the electrode icons 310 is assigned an integer (e.g., 1-18). A user can select or deselect an electrode icon 310 to respectively highlight or un-highlight the electrode icon 310 on the GUI 300. As will be discussed in more detail below, a selected electrode icon 310 will be designated to be an active electrode (e.g., a source electrode or a sink electrode). The user can select electrode icons 310 for particular paths of ablation. FIG. 4 shows an example graphical representation 306 of electrode icons 310 some of which are selected (i.e., electrodes 1-6, 12, and 16-18) to be active electrodes and the rest of the electrode icons 310 unselected such that ablation electrodes associated with such electrode icons will not be active during an ablation procedure.

The displayed real-time video 308 allows for visualization of an ablation procedure. The displayed real-time video 308 may include displaying video recorded by one or more cameras. For example, if an ablation catheter (e.g., the ablation catheter 200 of FIG. 2) includes four cameras, the real-time video 308 may display video recorded from each of the four cameras. In such embodiments, the real-time video 308 can display each of the four fields of view from the cameras overlaid with at least one other field of view.

The GUI 300 includes a number of icons (e.g., buttons, images, combinations thereof) that are associated with and can be used to control or monitor aspects of the ablation catheter and the GUI 300 itself.

FIG. 3 shows the GUI 300 including icons relating to the graphical representation 306 positioned in or near the first region 302 next to the graphical representation 306. For example, the GUI 300 includes three icons (i.e., an electrode selection icon 314, an electrode refresh icon 316, and a source-sink reverse icon 318) positioned next to the graphical representation 306 and that affect features of the ablation system 100. The electrode selection icon 314 can be used to select a pattern from a pre-determined menu of patterns of electrode icon selections 310 (e.g., inner ring of electrode icons 310, outer ring, all electrode icons 310, none). Once a pattern is selected, the selected electrode icons 310 can be highlighted on the GUI 300. The electrode refresh icon 316 can be used to unselect any electrode icon 310 that has been selected. The source-sink reverse icon 318 can be used in a bipolar mode to reverse which electrode icons 310 correspond to a sink and which electrode icons 310 correspond to a source.

FIG. 3 shows the GUI 300 including icons relating to the real-time video 308 positioned in or near the second region 304 next to the real-time video 308. For example, the GUI 300 includes three icons (i.e., a contrast icon 320, a luminosity icon 322, and a video refresh icon 324) positioned next to the real-time video 308 and that affect features of the real-time video 308. The contrast icon 320 can be used to increase or decrease contrast of the real-time video 308. The luminosity icon 322 can be used to modify illumination power of illumination sources in the ablation catheter. The video refresh icon 324 can be used to refresh the video feed and/or a display controller if the real-time video 308 encounters problems.

The GUI 300 includes a ribbon 326 with various icons relating to the ablation catheter and/or the GUI 300 itself. The ribbon 326 includes a status icon 328 indicating the system's status and a sonic/scan icon 330, which initiates a routine for initiating an ultrasonic source and for scanning the electrodes on the ablation catheter to identify potentially faulty electrodes. For example, the ablation catheter may be placed in a bath coupled to an ultrasonic source, and once the sonic/scan icon 330 is selected, the routine can turn on the ultrasonic source for a predetermined period of time to remove air bubbles stuck to the ablation catheter before a treatment procedure. After expiration of the predetermined period of time, the routine can sequentially activate all electrodes to determine whether any electrodes or RF amplifiers are defective. If the ultrasonic source is not connected, the sonic/scan icon 330 will just initiate the scanning portion of the routine.

The ribbon 326 also includes an in vivo icon 332, which can be selected to indicate that the ablation catheter has been placed within a patient; an anatomy icon 334, which can be used to identify the pulmonary vein (e.g., right superior, right inferior, left superior, left inferior) to be treated; a power icon 336, which displays and allows a user to modify, via arrow buttons, a power level at which the selected ablation electrodes will be energized; a procedure timing icon 338, which displays and allows a user to modify, via arrow buttons, the length of time the selected ablation electrodes are to be energized; an irrigation flow rate icon 340, which can be used to control flow rates of irrigation fluid through the ablation catheter; and a fluid volume icon 342, which indicates the amount of fluid passed through the ablation catheter since the in vivo icon 332 was selected. Once various selections are made via the icons, data associated the selections can be stored in a memory (e.g., the memory 118 and 130 of FIG. 1) and/or sent to a computing device (e.g., the computing device 124 of FIG. 1). For example, once a flow rate is selected, the selected flow rate can be sent to the computing device to control an irrigation fluid pump.

As described above, the GUI 300 allows a user to select, via the electrode icons 310, which electrodes on the ablation catheter will be active (e.g., either a source electrode or a sink electrode). The selected and highlighted electrode icons 310 indicate that, should an ablation procedure begin, only the ablation electrodes corresponding to the selected and highlighted electrode icons 310 will be active during the ablation procedure. FIG. 3 shows the GUI 300 including an ablation activate/deactivate icon 344 with text stating "Assign" or one or more similar terms. Once the "Assign" ablation activate/deactivate icon 344 has been selected, the "Assign" text for the ablation activate/deactivate icon 344 is replaced with "Ablate", "Start", or one or more similar terms.

When the ablation activate/deactivate icon 344 indicates "Assign" and is selected, a computing device assigns or designates the selected electrode icons 310 to be a source or a sink. For example, as shown in FIG. 4, electrode icons 310 numbered 1-6, 12, and 16-18 are selected, and FIG. 5 shows the selected electrode icons 310 as being either a source electrode or a sink electrode. In FIG. 5, the selected electrode icons 346 numbered "12", "2", "4", "6", and "17" are indicated as being source electrodes while the other selected electrode icons 348 (i.e., those numbered "1", "3", "5", "16", and "18") are indicated as being sink electrodes. In certain embodiments, the source electrodes are highlighted with a different color on the GUI 300 or are otherwise shown as being different than the sink electrodes.

FIG. 5 shows each of the source electrode icons 346 and the sink electrode icons 348 including icons indicating electrical units associated with the given electrode. For simplicity, the description below uses power in the form of Watts as the exemplary electrical unit displayed and modified via the GUI 300, but other electrical units (e.g., various forms of electrical energy) can be displayed and modified in place of power.

Figure 6:
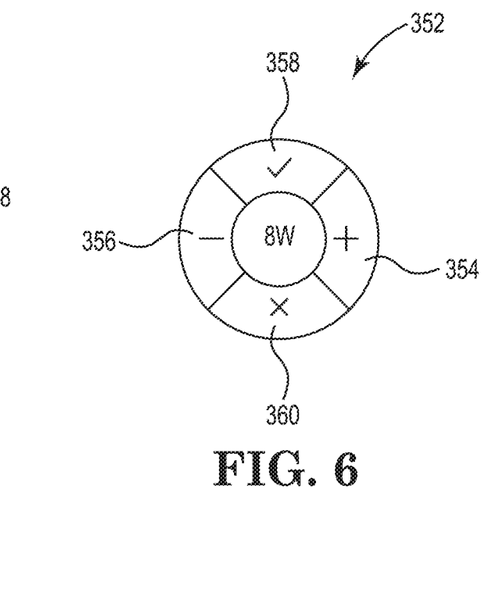
FIG. 6 shows an example power selection icon, in accordance with certain embodiments of the present disclosure.

FIG. 5 shows the source electrode icons 346 including a source power icon 350, which displays the power (e.g., 8 Watts) currently assigned to the corresponding ablation electrode. Each source power icon 350 can be selected to display a power selector icon 352, an example of which is shown in FIG. 6. The power selector icon 352 can cover the source power icon 350 on the GUI 300 until the user confirms or cancels changes in power.

The power selector icon 352 includes icons such as a power-increase icon 354 with a "+" sign for increasing the power associated with the given ablation electrode, a power-decrease icon 356 with a "−" sign for decreasing the power associated with the given ablation electrode, a power-confirmation icon 358 with a check-mark for confirming changes in power, and a power-cancellation icon 360 with an "X" for cancelling changes in power. The amount of power for each ablation electrode can be modified in real time. As power is increased or decreased for a given ablation electrode, the electrode icons 310 can be shaded or brightened to visually indicate that such electrode icons 310 have a different power.

FIG. 5 shows each of the sink electrodes 348 including a power estimation icon 362. Each of the power estimation icons 362 displays an estimated power associated with the given sink electrode 348. The estimated power displayed in the power estimation icons 362 is based at least in part on the power assigned to each of the source electrodes 346 and distances between the given sink electrode 348 and source electrodes 346. For example, a source electrode 346 will divide its energy among the sink electrodes 348 but more of its energy will be delivered to sink electrodes 348 positioned closer to the given source electrode 346.

Figure 7:
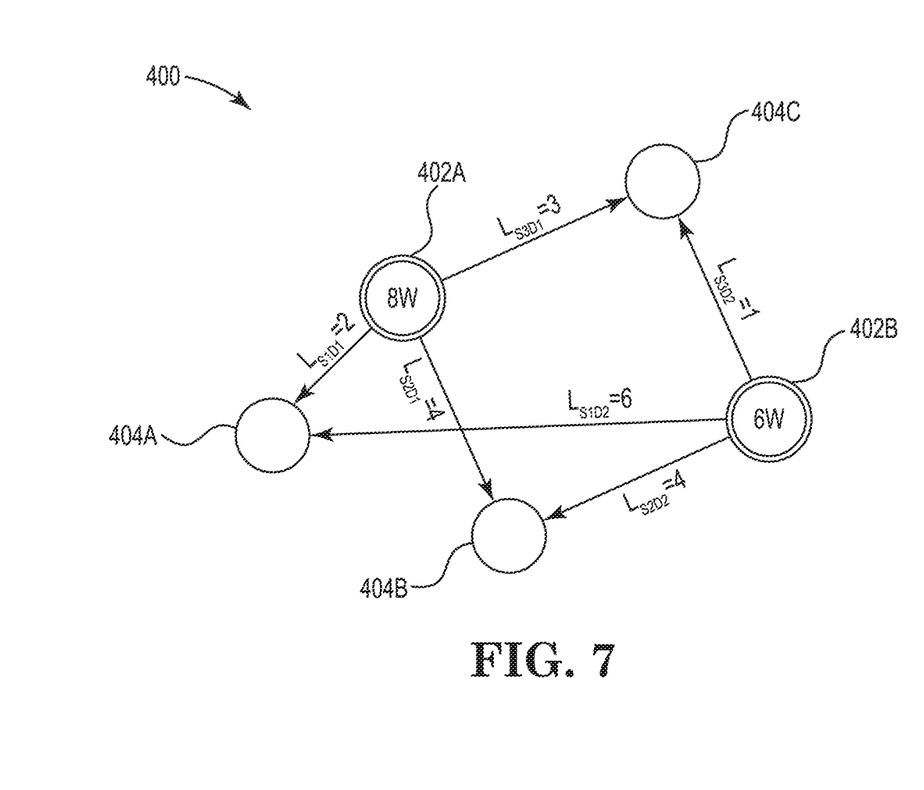
FIG. 7 shows a conceptual schematic of source electrodes and sink electrodes, in accordance with certain embodiments of the present disclosure.
Figure 8:
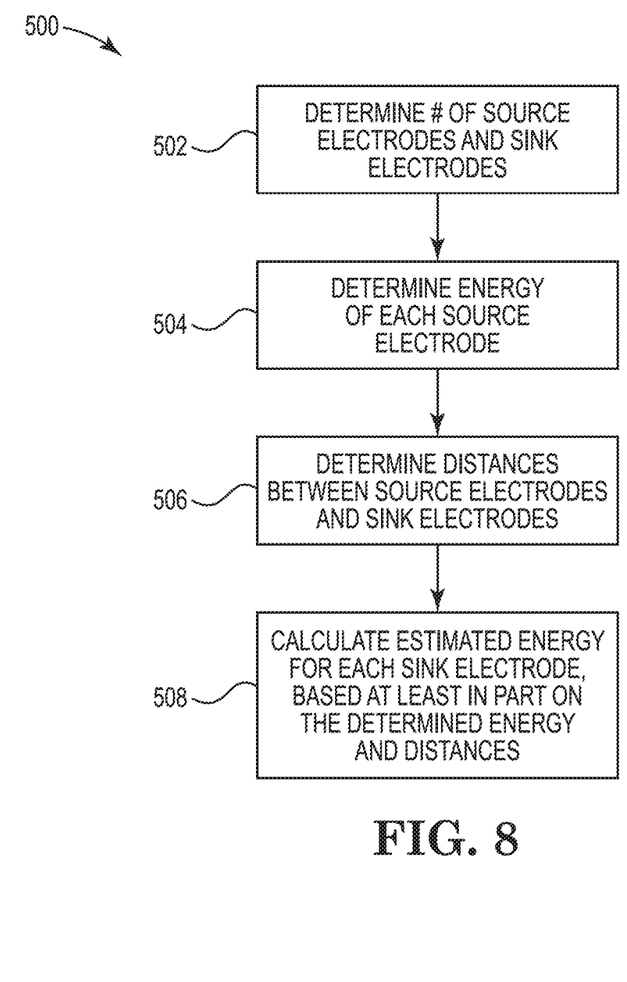
FIG. 8 shows a schematic of steps of estimating an amount of electrical units associated sink electrodes, in accordance with certain embodiments of the present disclosure.

FIG. 7 shows a schematic 400 of electrodes that helps illustrate how energy from source electrodes is estimated to contribute to energy received at sink electrodes, and FIG. 8 shows a schematic 500 of steps for estimating an amount of electrical units (e.g., energy, power) associated with each of the designated sink electrodes. The steps outlined in FIG. 8 and described below can be performed sequentially or in parallel and in various orders.

FIG. 8 shows a first step 502 of determining the number of source electrodes and the number of sink electrodes. The schematic 400 in FIG. 7 includes two source electrodes (i.e., a first source electrode 402A and a second source electrode 402B) and three sink electrodes (i.e., a first sink electrode 404A, a second sink electrode 404B, and a third sink electrode 404C). After determining the number of source electrodes and sink electrodes, FIG. 8 shows a step 504 of determining the assigned energy (e.g., power) for each of the source electrodes. The first source electrode 402A is associated with a power of 8 Watts, and the second source electrode 402B is associated with a power of 6 Watts. Step 506 involves determining the distances between each source electrode and each sink electrode. As shown in FIG. 7, the first source electrode 402A is positioned 2 units away from the first sink electrode 404A, 4 units from the second sink electrode 404B, and 3 units from the third sink electrode 404C. The second source electrode 402B is positioned 6 units away from the first sink electrode 404A, 4 units from the second sink electrode 404B, and 1 unit from the third sink electrode 404C.

The estimated energy to be received by the first sink electrode 404A, the second sink electrode 404B, and the third sink electrode 404C can be calculated based at least in part on the energy associated with each of the source electrodes and the distances between the source electrodes and the respective sink electrodes (step 508 in FIG. 8). Equation 1 is one example approach for calculating the estimated energy to be received by the sink electrodes, where $I_{S1}$ is the estimated energy at the first sink 404A, $L_{S1,Di}$=the distance between the sources and the first sink 404A, $L_{S2,Di}$=the distance between the sources and the second sink 404B, $L_{S3,Di}$=the distance between the sources and the third sink 404B, and $I_{Di}$=the sources' respective assigned energy.

$$I_{S1} = \sum_{i=1}^{2} \frac{L_{S1,Di}^{-1}}{L_{S1,Di}^{-1} + L_{S2,Di}^{-1} + L_{S3,Di}^{-1}} * I_{Di} \qquad \text{Equation 1}$$

As shown in Equation 1, the estimated power for each sink electrode is a summation of each source electrode's contribution to power at the sink electrode. When each of the source electrodes is assigned the same amount of power, the source electrode positioned farthest from a given sink electrode will be estimated to contribute the least to the power of the given sink electrode.

In certain embodiments, distances between source electrodes and sink electrodes are based on arc-length distances between edges (e.g., edge-to-edge distances) of the respective electrodes (e.g., energy delivery elements 204 of FIG. 2) when the expandable member 202 is substantially deployed (e.g., substantially fully expanded). FIG. 2 includes three examples of edge-to-edge distances (i.e., D1, D2, and D3) between electrodes. The edge-to-edge distances are arc-length distances to account for the curved shape of the expandable member 202 when fully deployed. In certain embodiments, the distances are predetermined distances stored in a table and accessed by the system. In other embodiments, the distances between source electrodes and sink electrodes are computed. For example, the electrodes may include position tracking features or be capable of sensing signals such that the distances between the electrodes can be computed in real time. In such embodiments, the geometry of the electrodes may be stored in a table and accessed by the system.

In certain embodiments, the estimated power displayed in each of the power estimation icons 362 is updated as a user modifies power assigned for a given source electrode 346 or as more electrodes are designated as being inactive or active (and therefore a source electrode or a sink electrode).

In certain embodiments, the estimated power for each of the source electrodes 348 is compared to one or more thresholds. Different thresholds can be associated with different sets of sink electrodes 348 (e.g., proximal electrodes, distal electrodes). If the estimated power for a given source electrode 348 is above a predetermined threshold, the GUI 300 can indicate that the threshold is violated. For example, if one or more source electrodes 348 are estimated to receive power above the threshold, the GUI 300 can display a warning message or alarm and/or can display the power estimation icon 362 associated with the violating sink electrode 348 in a different color (e.g., red) than the power estimation icons 362 associated with the other sink electrodes 348. In FIG. 5, the power estimation icon 362 is shown as being displayed differently than the other power estimation icon 362 to indicate that a threshold has been breached. In certain embodiments, if the power estimated at one of the sink electrodes 348 violates the threshold, the system 100 will not be able to initiate an ablation procedure. For example, so long as one of the estimated power amounts violates the threshold, certain icons on the GUI 300 for initiating energy delivery to the ablation catheter (e.g., the ablation activate/deactivate icon 344) can be disabled. The disabled ablation icon(s) can be enabled once all of the estimated power amounts are below respective thresholds. As noted above, the power estimates can be updated dynamically as power, etc., is modified by the user.

In certain embodiments, upon selecting the ablation activate/deactivate icon 344 or another icon on the GUI 300, the source electrodes 346 are automatically assigned an amount of power in accordance with certain goals. In one example, the source electrodes 346 are assigned a power such that an estimated power associated with each of the designated sink electrodes 348 is less than a predetermined threshold (e.g., 10 Watts, 11 Watts). As described above, different thresholds can be applied to different sets of sink electrodes 348 such that estimated power for each of the proximal sink electrodes are compared against a different threshold than the distal sink electrodes. In another example, the source electrodes 346 are assigned a power such that an estimated power associated with each of the designated sink electrodes 348 such that the estimated power for each of the designated sink electrodes is substantially similar (e.g., within 5%, within 10%) to the estimated power of the other sink electrodes. When the sink electrodes 348 have similar estimated powers, it is more likely that lesions created by the ablation catheter will be more uniform (e.g., lesions with same or similar depth along the lesion).

Once the user sets the desired power for each of the source electrodes 346 (e.g., assisted by viewing the estimated power amounts for the sink electrodes 348), the user can select the ablation activate/deactivate icon 344. Selecting the ablation activate/deactivate icon 344 initiates and/or stops energy delivery to the ablation electrodes of the ablation catheter. Once the activate/deactivate icon 344 is pressed to initiate energy delivery, a graphic in the activate/deactivate icon 344 changes (e.g., changes to a stop sign). Further, once the activate/deactivate icon 344 is selected to initiate energy delivery, a signal is transmitted to an RF generator (e.g., the RF generator 114 of FIG. 1) and/or an RF generator controller (e.g., the RF generator controller 116 of FIG. 1) to start delivering energy to the selected ablation electrodes of the ablation catheter.

The various methods and functions described above can be carried out by components discussed above, for example, computing devices with one or more controllers implemented using firmware, integrated circuits, and/or software modules that interact with each other or are combined together. The controllers may include memory storing computer-readable instructions/code (e.g., computer program products) for execution by a processor to perform aspects discussed herein.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:
1. An ablation system comprising:
a radiofrequency (RF) generator configured to generate RF energy;
an ablation catheter in communication with the RF generator and including a plurality of electrodes; and
one or more controllers in communication with the RF generator and configured to:
generate a graphical representation of the plurality of electrodes of the ablation catheter for displaying via a graphical user interface (GUI),
designate, via the GUI, at least some of the plurality of electrodes to be active electrodes,
designate the active electrodes as a source electrode or a sink electrode, at least two or more active electrodes of the active electrodes being designated as source electrodes and at least two or more active electrodes of the active electrodes being designated as sink electrodes,
assign an amount of power to each designated source electrode of the designated source electrodes, and
estimate an amount of power associated with each designated sink electrode of the designated sink electrodes based at least in part on the assigned amount of power of each designated source electrode of the designated source electrodes,
wherein the estimated amount of power associated with each sink electrode of the designated sink electrodes is further based at least in part on distances between the designated source electrodes and the designated sink electrodes.

2. The ablation system of claim 1, wherein the distances between the designated source electrodes and the designated sink electrodes represent edge-to-edge distances.

3. The ablation system of claim 1, wherein the distances are selected from a table of predetermined distances stored in the one or more controllers or computed by the one or more controllers.

4. The ablation system of claim 1, wherein the estimated amount of power associated with each designated sink electrode of the designated sink electrodes is based at least in part on adding each designated source electrode's contribution to power associated with each designated sink electrode of the designated sink electrodes.

5. The ablation system of claim 1, wherein the one or more controllers is configured to:
modify the assigned amount of power to at least one of the designated source electrodes or designate an additional electrode as an active electrode or inactive electrode; and
re-estimate the estimated amount of power associated with each designated sink electrode of the designated sink electrodes based at least in part on the modified assigned amount of power of the at least one designated source electrode or the additional active electrode or inactive electrode.

6. The ablation system of claim 5, wherein the one or more controllers is configured to:
determine that the estimated amount of power associated with at least one of the designated sink electrodes is above a threshold; and
disable an ablation-initiation button on the GUI in response to the determination.

7. The ablation system of claim 6, wherein the one or more controllers is configured to:
after re-estimating the amount of power associated with each designated sink electrode of the designated sink electrodes, determine that the estimated power associated with at least one of the designated sink electrodes is below the threshold; and
enable the ablation-initiation button on the GUI in response to determining that the estimated power associated with at least one of the designated sink electrodes is below the threshold.

8. The ablation system of claim 1, wherein the ablation catheter includes an expandable member carrying the plurality of electrodes.

9. The ablation system of claim 1, further comprising:
a display in communication with the one or more controllers and configured to display the GUI.

10. A computing device for generating and using a graphical user interface (GUI), the computing device comprising:
one or more controllers configured to:
generate a graphical representation of a plurality of electrodes of an ablation catheter for displaying via the GUI,
designate, via the GUI, at least some of the plurality of electrodes to be active electrodes,
automatically designate the active electrodes as a source electrode or a sink electrode, at least two or more active electrodes of the active electrodes being designated as source electrodes and at least two or more active electrodes of the active electrodes being designated as sink electrodes,
assign an amount of energy to each designated source electrode of the designated source electrodes, and
estimate an amount of energy associated with each designated sink electrode of the designated sink electrodes based at least in part on the assigned amount of energy of each designated source electrode of the designated source electrodes,
wherein the estimated amount of energy associated with each designated sink electrode of the designated sink electrodes is further based at least in part on distances between the designated source electrodes and the designated sink electrodes.

11. The computing device of claim 10, wherein the distances between the designated source electrodes and the designated sink electrodes represent edge-to-edge distances.

12. The computing device of claim 10, wherein the distances are selected from a table of predetermined distances stored in the one or more controllers.

13. The computing device of claim 10, wherein the estimated amount of energy associated with each designated sink electrode of the designated sink electrodes is based at least in part on adding each designated source electrode's contribution to energy associated with each designated sink electrode of the designated sink electrodes.

14. The computing device of claim 10, wherein the one or more controllers includes a computer readable storage medium having program code stored thereon for execution by the one or more controllers.

15. The computing device of claim 10, wherein the one or more controllers is configured to:
determine that the estimated amount of energy associated with at least one of the designated sink electrodes is above a threshold; and
disable an ablation-initiation button on the GUI in response to the determination.

16. A computing device for generating and using a graphical user interface (GUI), the computing device comprising:
one or more controllers configured to:
generate a graphical representation of a plurality of electrodes of an ablation catheter for displaying via the GUI,
designate, via the GUI, at least some of the plurality of electrodes to be active electrodes,
automatically designate the active electrodes as a source electrode or a sink electrode, at least two or more active electrodes of the active electrodes being designated as source electrodes and at least two or more active electrodes of the active electrodes being designated as sink electrodes, and
automatically assign an amount of power to each designated source electrode of the designated source electrodes such that an estimated amount of power associated with each sink electrode of the designated sink electrodes is less than a first predetermined threshold,
wherein an estimated amount of power of a first set of the designated sink electrodes is compared against the first predetermined threshold, wherein an estimated amount of power of a second set of the designated sink electrodes is compared against a second predetermined threshold that is different than the first predetermined threshold.

17. The computing device of claim 16, wherein the one or more controllers are further configured to:

automatically assign an amount of power to each designated source electrode of the designated source electrodes such that an estimated amount of power associated with a first sink electrode of the designated sink electrodes is substantially similar to an estimated amount of power of a second sink electrode of the designated sink electrodes.

\* \* \* \* \*